United States Patent [19]

Behlke

[11] 4,216,891
[45] Aug. 12, 1980

[54] SURGICAL STAPLER

[76] Inventor: Harold O. Behlke, 4060 Toenges, St. Louis, Mo. 63116

[21] Appl. No.: 11,304

[22] Filed: Feb. 12, 1979

[51] Int. Cl.² ............................................. B25C 5/02
[52] U.S. Cl. ........................................ 227/30; 227/19
[58] Field of Search .................... 227/19, 30, 135, 152

[56] References Cited
U.S. PATENT DOCUMENTS

| 3,494,533 | 2/1970 | Green et al. | 227/19 |
| 3,589,589 | 6/1971 | Akopov | 227/19 |
| 3,795,034 | 3/1974 | Strekopytov et al. | 227/19 |
| 3,935,981 | 2/1976 | Akopov et al. | 227/19 |

Primary Examiner—John McQuade
Attorney, Agent, or Firm—Cohn, Powell & Hind

[57] ABSTRACT

A surgical stapler having a jaw including spaced apart front and rear legs rigidly interconnected by a cross leg at one end and having opposite free ends. An anvil is mounted on the front leg. A movable frame is located between the front and rear legs and carries a staple cartridge assembly. The position of the movable frame determines the gap between the staple cartridge assembly and the anvil for receiving tissue. A pusher member ejects staples from the staple cartridge assembly to staple tissue located in the gap. A C-clamp is detachably connected to the free ends of the front and rear legs of the jaw for maintaining alignment of the front and rear legs during the stapling operation.

12 Claims, 4 Drawing Figures

SURGICAL STAPLER

BACKGROUND OF THE INVENTION

This invention relates to a surgical stapler for stitching body organs. A surgical stapler of this general type is described in U.S. Pat. No. 3,494,533.

It is necessary to maintain the front and rear jaw legs in alignment so that the staple cartridge and anvil are properly aligned for stapling operation. In the device described in the U.S. Pat. No. 3,494,533, a pin extends through the rear leg and into the front leg of the jaw to maintain this alignment. When it is desired to staple tissue which has one end extending beyond the end of the gap between the staple cartridge and the anvil, the tissue will be punctured by the jaw-aligning pin when the pin is inserted. This punctured tissue requires additional surgical procedures, and could result in medical complications.

SUMMARY OF THE INVENTION

This surgical stapler enables stapling of tissue without perforating the tissue which may extend beyond the end of the gap between the staple cartridge and the anvil by the means used to maintain alignment of the jaw legs and alignment of the staple cartridge assembly and the anvil.

The surgical stapler has a jaw which includes spaced apart front and rear legs rigidly interconnected by a cross leg at one end, the front and rear legs having opposite free ends. An anvil is on the front leg, while a movable frame is located between the front and rear legs. A staple cartridge assembly including staples is carried by the movable frame. The position of the movable frame determines a gap between the staple cartridge assembly and the anvil for receiving tissue. A pusher member is included for ejecting staples from the staple cartridge assembly to staple tissue located in the gap between the cartridge assembly and the anvil. A C-clamp is detachably connected to the free ends of the front and rear legs of the jaw for maintaining alignment of the front and rear legs during stapling operation.

In one aspect of the invention, the C-clamp includes a first end engaging the free end of the front leg, and a second end engaging the free end of the rear leg, while an integral web interconnects the first and second ends. A first jaw-aligning means fixes the first end of the C-clamp to the front leg, and a second jaw-aligning means fixes the second end of the C-clamp to the rear leg.

In one aspect of the invention, the C-clamp is fixed to the jaw with the C-clamp and the jaw in the same plane. The web of the C-clamp is spaced from the free ends of the legs of the jaw for accommodating tissue extending outwardly of the gap between the staple cartridge assembly and the anvil.

In one aspect of the invention, the first jaw-aligning means includes a first alignment pin. The first end of the C-clamp engages the outside of the front leg. The first alignment pin is attached to the first leg of the C-clamp with the alignment pin extending into a hole in the front leg for aligning the first end of the C-clamp with the front leg of the jaw.

In one aspect of the invention, the second end of the C-clamp engages the outside of the rear leg. The second jaw-aligning means includes a sleeve on the second end of the C-clamp, the sleeve being received in a slot in the rear leg and being detachably connected to the rear leg of the jaw for aligning the second end of the C-clamp with the rear leg of the jaw. More particularly, the second end of the C-clamp is bifurcated having spaced arms between which the sleeve extends, one of the arms engaging the outside of the rear leg.

In one aspect of the invention, a second alignment pin is detachably connected to the second end of the C-clamp, and extends through the movable frame and into the staple cartridge assembly for maintaining alignment of the staple cartridge assembly relative to the anvil. The second alignment pin includes an end that terminates within the staple cartridge assembly for preventing injury to the tissue in the gap between the staple cartridge assembly and the anvil. The second alignment pin is attached to and extends through the sleeve. More particularly, the first and second alignment pins are coaxial. The front and rear legs of the jaw are aligned without puncturing the tissue in the gap by either of the first and second alignment pins during stapling of the tissue.

DESCRIPTION OF THE PREFERRED EMBODIMENT

Figure 1:
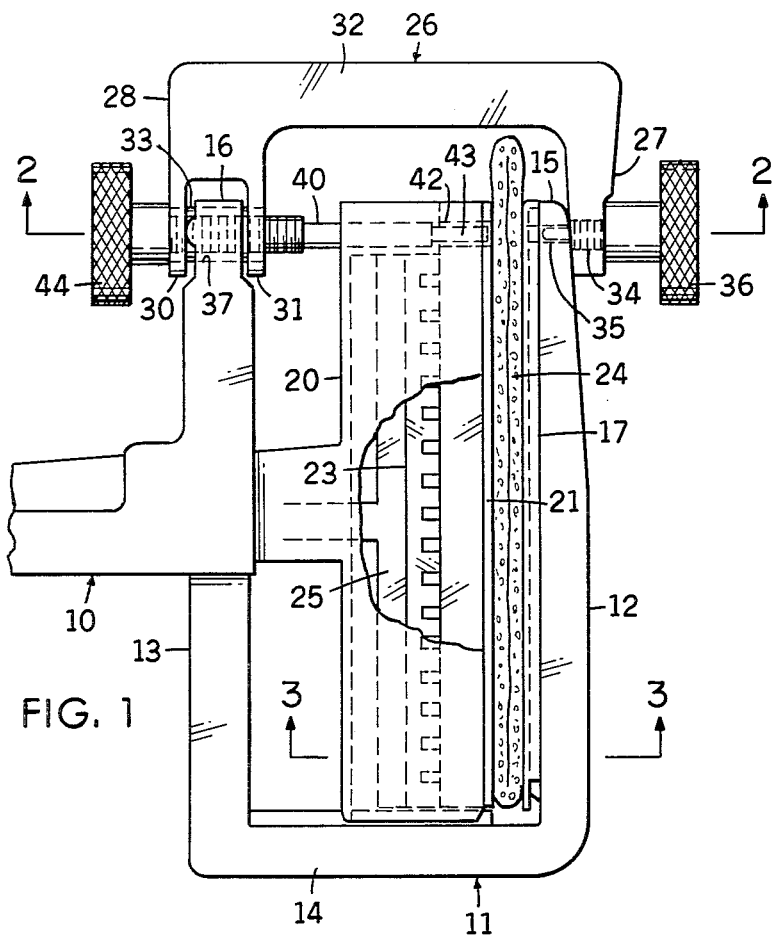
FIG. 1 is a fragmentary side elevation view of the jaw end of the surgical stapler.
Figure 2:
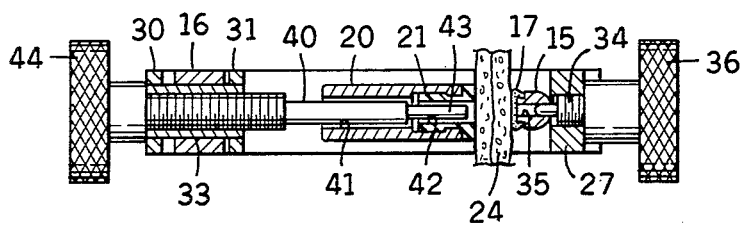
FIG. 2 is a cross-sectional view taken on line 2—2 of FIG. 1.
Figure 3:
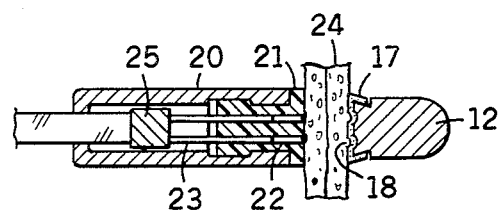
FIG. 3 is an enlarged cross-sectional view taken on line 3—3 of FIG. 1.
Figure 4:
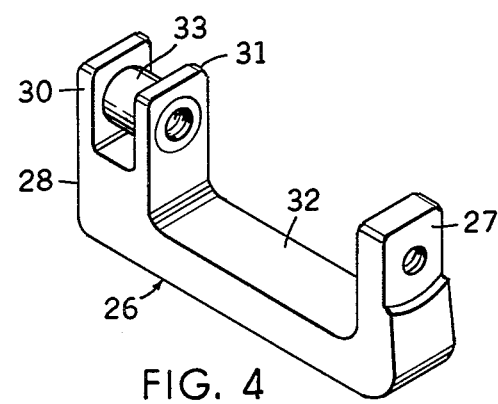
FIG. 4 is a perspective view of the C-clamp.

The surgical stapler in which the present improvements are utilized, is fully disclosed in U.S. Pat. No. 3,494,533, issued Feb. 10, 1970 to D. T. Green et al, and this disclosure is incorporated herein as if fully shown in the drawings and described in the specification.

The surgical stapler indicated generally by 10 has a jaw indicated generally by 11. The jaw 11 includes spaced apart front and rear legs 12 and 13 respectively. Rigidly interconnecting the front and rear legs 12 and 13 is a cross leg 14, the opposite ends 15 and 16 of the legs 12 and 13 respectively being free.

An anvil 17 is located on the inside of the front leg 12, the anvil 17 including two longitudinal rows of staple-receiving and forming grooves 18. Located between the legs 12 and 13 is a movable frame 20. The movable frame 20 carries a staple cartridge assembly 21, which includes two longitudinal rows of staples 22 and staples drivers 23, the staples 22 being aligned with anvil grooves 18.

The position of the movable frame 20 determines a gap between the staple cartridge assembly 21 and the anvil 17 for receiving tissue 24. The mechanism for adjusting the position of movable frame 20 is fully disclosed in U.S. Pat. No. 3,494,533 and is incorporated herein.

A pusher member 25 engages the staple drivers 23, and is moved to eject the staples 22 from the staple cartridge assembly 21 to staple tissue 24 located in the gap between the staple cartridge assembly 21 and the anvil 17. The mechanism for operating the pusher member 25 is fully disclosed in U.S. Pat. No. 3,494,533 and is incorporated herein.

A C-clamp indicated generally by 26 is detachably connected to the free ends 15 and 16 of the front and rear legs 12 and 13 respectively of the jaw 11 for maintaining alignment of the front and rear legs 12 and 13 during stapling operation. The C-clamp 26 includes a first end 27 and a second end 28 which is bifurcated having spaced arms 30 and 31. A web 32 interconnects the first and second ends 27 and 28. A sleeve 33 extends between the arms 30 and 31 of the second end 28. The web 32 is spaced from the free ends 15 and 16 of the front and rear legs 12 and 13 for accommodating tissue 24 extending outwardly of the gap between the staple cartridge assembly 21 and the anvil 17. Preferably, the jaw 11 and the C-clamp 26 are located in the same plane.

A first jaw-aligning means includes a first alignment pin 34 which is threadedly attached to the first end 27 of the C-clamp 26 and extends into a hole 35 in the front leg 12, while the first end 27 engages the outside of the free end 15 of the front leg 12. The C-clamp 26 maintains alignment of the front and rear legs 12 and 13 during stapling operation. A first knob 36 is attached to the first alignment pin 34 to facilitate threadable attachment and detachment of the alignment pin 34 and the first end 27.

The second end 28 engages the outside of the rear leg 13 at the arm 30. The rear leg 13 includes a slot 37 into which the sleeve 33 is received, thereby detachably connecting the rear leg 13 with the second end 28 of the C-clamp 26. This detachable connection constitutes a second jaw-aligning means.

A second alignment pin 40 is threadedly attached to and extends through the sleeve 33. This second alignment pin 40 is coaxial with the first alignment pin 34. The second alignment pin 40 extends through a hole 41 in the movable frame 20 and into a hole 42 in the staple cartridge assembly 21 for maintaining alignment of the staple cartridge assembly 21 relative to the anvil 17, and therefore maintaining alignment of the staples 22 and cooperating anvil grooves 18. An end 43 of the second alignment pin 40 terminates within the staple cartridge assembly 21 for preventing injury to the tissue 24 in the gap between the staple cartridge assembly 21 and the anvil 17. A second knob 44 is attached to the second alignment pin 40 to facilitate threadable attachment and detachment of the alignment pin 40 and the sleeve 33.

It is thought that the structural features and functional advantages of this device have become fully apparent from the foregoing description of parts, but for completeness of disclosure the operation of this device will be briefly discussed.

When it is desired to staple tissue 24, the jaw 11 is placed around the tissue 24 to be stapled. The C-clamp 26 is placed on the open end of the jaw 11 with the tissue 24 extending beyond the ends of the staple cartridge assembly 21 and the anvil 17 the tissue 24 extending into the area between the free ends 15 and 16 of the legs 12 and 13 and the web 32. The second clamp end 28 is positioned around the free end 16 of the rear jaw leg 13 with the sleeve 33 being received in the slot 37, the arm 30 engaging the outside of the rear jaw leg 13, while the first clamp end 27 engages the outside of the front jaw leg 12. The pin 34 is inserted into the first clamp end 27 and is threadably attached with the pin 34 extending into the hole 35 of the front jaw leg 12. The second alignment pin 40 is threadably inserted in the sleeve 33 and is extended through the hole 41 of the movable frame 20 and into hole 42 of the staple cartridge assembly 21 to provide alignment of the staple cartridge assembly 21 and the anvil 17 during stapling operation. The movable frame 20 is adjusted by means fully disclosed in U.S. Pat. No. 3,494,533 and incorporated by reference, to provide a proper gap between the staple cartridge assembly 21 and the anvil 17.

The pusher member 25 is then moved into engagement with the staple drivers 23 by means fully disclosed in U.S. Pat. No. 3,494,533 and incorporated by reference, causing the staples 22 to be ejected from the staple cartridge assembly 21, the staples 22 extending through the tissue 24 and being effectively formed and closed by the cooperating groove 18 of the anvil 17.

The tissue 24 can then be removed from the stapler 10. The pusher member 25 is withdrawn, and the movable frame 20 is moved away from the tissue 24. The alignment pins 34 and 40 are removed, and the C-clamp 26 is then disengaged from the jaw 11, allowing the tissue 24 to be removed from the stapler 10. The stapler 10 can then be reloaded with a new staple cartridge assembly 21, and used for further stapling operation or can then be cleaned for future use.

I claim as my invention:

1. In a surgical stapler:
   (a) a jaw including spaced apart front and rear legs rigidly interconnected by a cross leg at one end and having opposite free ends,
   (b) an anvil on the front leg,
   (c) a movable frame located between the front and rear legs,
   (d) a staple cartridge assembly, including staples, carried by the movable frame, the movable frame determining a gap between the staple cartridge assembly and anvil for receiving tissue,
   (e) a pusher member for ejecting staples from the staple cartridge assembly to staple tissue located in the gap between the staple cartridge assembly and anvil, and
   (f) a C-clamp detachably connected to the free ends of the front and rear legs of the jaw for maintaining alignment of the front and rear legs during stapling operation.

2. A surgical stapler as defined in claim 1, in which:
   (g) the C-clamp includes:
      1. a first end engaging the free end of the front leg,
      2. a second end engaging the free end of the rear leg, and
      3. an integral web interconnecting the first and second ends,
   (h) a first jaw-aligning means fixing the first end of the C-clamp to the front leg, and
   (i) a second jaw-aligning means fixing the second end of the C-clamp to the rear leg, the C-clamp maintaining alignment of the front and rear legs during stapling operation.

3. A surgical stapler as defined in claim 1, in which:
   (g) the C-clamp is fixed to the jaw with the C-clamp and the jaw in the same plane, and
   (h) the web of the C-clamp is spaced from the free ends of the legs of the jaw for accommodating tissue extending outwardly of the gap between the staple cartridge assembly and the anvil.

4. A surgical stapler as defined in claim 2, in which:
   (j) the first jaw-aligning means includes a first alignment pin, and
   (k) the first end of the C-clamp engages the outside of the front leg, the front leg being provided with a hole, the first jaw-aligning means being attached to the first end of the C-clamp with the first alignment pin extending into the hole in the front leg for aligning the first end of the C-clamp with the front leg of the jaw.

5. A surgical stapler as defined in claim 2, in which:
(j) the second end of the C-clamp engages the outside of the rear leg, the rear leg includes a slot, and
(k) the second jaw-aligning means includes a sleeve on the second end of the C-clamp, the sleeve being received in the leg slot and detachably connected to the rear leg of the jaw for aligning the second end of the C-clamp with the rear leg of the jaw.

6. A surgical stapler as defined in claim 5, in which:
(1) the second end of the C-clamp is bifurcated having spaced arms between which the sleeve extends, one of the arms engaging the outside of the rear leg.

7. A surgical stapler as defined in claim 5, in which:
(1) an alignment pin is detachably connected to the second end of the C-clamp, and extends through the movable frame and into the staple cartridge assembly for maintaining alignment of the staple cartridge assembly relative to the anvil.

8. A surgical stapler as defined in claim 7, in which:
(m) the alignment pin includes an end that terminates within the staple cartridge assembly for preventing injury to the tissue in the gap between the staple cartridge assembly and the anvil.

9. A surgical stapler as defined in claim 8, in which:
(n) the alignment pin is threadedly attached to and extends through the sleeve.

10. A surgical stapler as defined in claim 2, in which:
(j) the first jaw-aligning means includes a first alignment pin,
(k) the first end of the C-clamp engages the outside of the front leg, the front leg being provided with a hole, the first jaw-aligning means being threadedly attached to the first end of the C-clamp with the first alignment pin extending into the hole in the front leg for aligning the first end of the C-clamp with the front leg of the jaw,
(l) the second end of the C-clamp engages the outside of the rear leg, the rear leg includes a slot, and
(m) a second alignment pin is detachably connected to the second end of the C-clamp and extends through the movable frame and into the staple cartridge assembly for maintaining alignment of the staple cartridge assembly relative to the anvil.

11. A surgical stapler as defined in claim 10, in which:
(n) the first and second alignment pins are coaxial.

12. A surgical stapler as defined in claim 2, in which:
(j) the C-clamp is fixed to the jaw with the C-clamp and the jaw in the same plane,
(k) the web of the C-clamp is spaced from the free ends of the legs of the jaw for accommodating tissue extending outwardly of the gap between the staple cartridge assembly and the anvil,
(l) the first jaw-aligning means includes a first alignment pin,
(m) the first end of the C-clamp engages the outside of the front leg, the front leg being provided with a hole, the first jaw-aligning means being threadedly attached to the first end of the C-clamp with the first alignment pin extending into the hole in the front leg for aligning the first end of the C-clamp with the front leg of the jaw,
(n) the second end of the C-clamp engages the outside of the rear leg, the rear leg includes a slot,
(o) the second end of the C-clamp is bifurcated having spaced arms and a sleeve extending between the spaced arms, one of the arms engaging the outside of the rear leg,
(p) a second alignment pin is detachably connected to the second end of the C-clamp, and extends through the movable frame and into the staple cartridge assembly for maintaining alignment of the staple cartridge assembly relative to the anvil, the second alignment pin including an end that terminates within the staple cartridge assembly for preventing injury to the tissue, in the gap between the staple cartridge assembly and anvil, and the second alignment pin is threadedly attached to and extends through the sleeve, and
(q) the first and second alignment pins are coaxial.

* * * * *